United States Patent
Tsuchimoto et al.

(10) Patent No.: US 9,360,365 B2
(45) Date of Patent: Jun. 7, 2016

(54) OPTICAL SENSOR DEVICE FOR DETECTING A PULSE OF A LIVING BODY

(71) Applicant: MURATA MANUFACTURING CO., LTD., Nagaokakyo-Shi, Kyoto-fu (JP)

(72) Inventors: Hirofumi Tsuchimoto, Nagaokakyo (JP); Toru Shimuta, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 159 days.

(21) Appl. No.: 14/083,904

(22) Filed: Nov. 19, 2013

(65) Prior Publication Data

US 2014/0070077 A1 Mar. 13, 2014

Related U.S. Application Data

(63) Continuation of application No. PCT/JP2012/055967, filed on Mar. 8, 2012.

(30) Foreign Application Priority Data

May 20, 2011 (JP) ................................. 2011-113482
May 20, 2011 (JP) ................................. 2011-113485

(51) Int. Cl.
*H03F 3/08* (2006.01)
*G01J 1/44* (2006.01)
(Continued)

(52) U.S. Cl.
CPC ............... *G01J 1/44* (2013.01); *A61B 5/14552* (2013.01); *G01J 3/427* (2013.01); *G01N 21/256* (2013.01);
(Continued)

(58) Field of Classification Search
CPC .................................................. A61B 5/14552
USPC ....................................................... 250/214 A
See application file for complete search history.

(56) References Cited

U.S. PATENT DOCUMENTS 4,846,183 A * 7/1989 Martin ............... G01N 21/3151
356/41
5,355,882 A 10/1994 Ukawa et al.
(Continued)

FOREIGN PATENT DOCUMENTS

CN 1335756 A 2/2002
CN 101455567 A 6/2009
(Continued)

OTHER PUBLICATIONS

International Search Report and Written Opinon of PCT/JP2012/055967, date of mailing Jun. 12, 2012.
(Continued)

*Primary Examiner* — Thanh Luu
(74) *Attorney, Agent, or Firm* — Arent Fox LLP

(57) ABSTRACT

An optical sensor device includes a light emitter for emitting, to a living body, lights having two wavelengths and blinking at a predetermined frequency, and a light receiver for receiving the lights from the living body. The light receiver outputs first and second detection signals corresponding to the respective wavelengths. A filter circuit extracts, from the first and second detection signals, modulation signals that are obtained with amplitude modulation of signals of the predetermined frequency. The modulation signals are amplified by a post-amplifier and are taken into an arithmetic processing unit after being converted to digital signals by an AD converter. The arithmetic processing unit calculates DC components and AC components of the first and second detection signals by employing the modulation signals converted the digital signals.

15 Claims, 10 Drawing Sheets

(51) Int. Cl.
*G01J 3/427* (2006.01)
*G01N 21/25* (2006.01)
*G01N 21/31* (2006.01)
*A61B 5/1455* (2006.01)
*A61B 5/00* (2006.01)

(52) U.S. Cl.
CPC ........... *G01N 21/3151* (2013.01); *A61B 5/6826* (2013.01); *A61B 5/6829* (2013.01); *A61B 5/7203* (2013.01)

(56) References Cited

U.S. PATENT DOCUMENTS

| | | | |
|---|---|---|---|
| 6,163,715 | A | 12/2000 | Larsen et al. |
| 6,453,184 | B1 | 9/2002 | Hyogo et al. |
| 6,922,577 | B2 | 7/2005 | Nakashima et al. |
| 7,229,414 | B2 | 6/2007 | Satoh et al. |
| 2003/0158486 | A1 | 8/2003 | Nakashima et al. |
| 2004/0210142 | A1 | 10/2004 | Satoh et al. |
| 2005/0250998 | A1* | 11/2005 | Huiku ............ A61B 5/1495 600/331 |
| 2010/0222658 | A1* | 9/2010 | Cheng ............ A61B 5/6833 600/324 |

FOREIGN PATENT DOCUMENTS

| | | |
|---|---|---|
| JP | 02-013815 A | 1/1990 |
| JP | 3-86152 A | 4/1991 |
| JP | 5-176901 A | 7/1993 |
| JP | H06-22943 A | 2/1994 |
| JP | H06-169892 A | 6/1994 |
| JP | 7-124138 A | 5/1995 |
| JP | 3116252 B | 10/2000 |
| JP | 2001-78990 A | 3/2001 |
| JP | 2003-240716 A | 8/2003 |
| JP | 2004-313409 A1 | 11/2004 |

OTHER PUBLICATIONS

Chinese Office Action issued for counterpart application No. CN201280024346.4, date of dispatch Nov. 2, 2014 (with English translation).

Wang Rongfang; Thesis for Master Degree of Engineering of Beijing University of Technology, "Research and Development in Reflectance Oxygen Saturation Detecting System", Dec. 31, 2002.

* cited by examiner

OPTICAL SENSOR DEVICE FOR DETECTING A PULSE OF A LIVING BODY

CROSS REFERENCE TO RELATED APPLICATIONS

The present application is a continuation of PCT/JP2012/055967 filed Mar. 8, 2012, which claims priority to Japanese Patent Application No. 2011-113482, filed May 20, 2011, and to Japanese Patent Application No. 2011-113485, filed May 20, 2011, the entire contents of each of which are incorporated herein by reference.

FIELD OF THE INVENTION

The present invention relates to an optical sensor device including a light emitter and a light receiver.

BACKGROUND OF THE INVENTION

In general, there is known an optical sensor device of the type including a light emitter for emitting light to a measurement target, and a light receiver for receiving the light having been reflected by or transmitted through a living body (see, e.g., Patent Documents 1 and 2). Patent Document 1 discloses a technique of illuminating a finger or an earlobe of a living body with light emitted from a light emitter, receiving the light having been reflected by or transmitted through the living body by a light receiver, and detecting a photo-plethysmographic signal corresponding to the pulse of the living body based on an electrical signal output from the light receiver. In the technique of Patent Document 1, an amplifier is connected to the light receiver in order to amplify the electrical signal obtained through photoelectric conversion performed by the light receiver, and the amplified electrical signal is input to a processor to execute various types of signal processing.

Patent Document 2 discloses a technique of reflecting light from a reference light source by a scanning mirror, and receiving the reflected light by a detection element. In the technique of Patent Document 2, a signal from the detection element is separated into a direct current (DC) component and an alternating current (AC) component, each of which is converted to a digital signal by an AD converter.

Patent Document 1: Japanese Unexamined Patent Application Publication No. 6-22943
Patent Document 2: Japanese Unexamined Patent Application Publication No. 2-13815

In the optical sensor device disclosed in Patent Document 1, the electrical signal output from the light receiver is amplified by the amplifier. At that time, because extraneous light, such as the sunlight, enters the light receiver in some cases, a noise component attributable to the extraneous light may be superimposed on the electrical signal. If the noise component attributable to the extraneous light becomes excessive, the amplifier would be saturated and a signal corresponding to the light emitted from the light emitter, such as a photo-plethysmographic signal, would not be detected correctively. Furthermore, if an amplification degree of the amplifier is reduced to prevent the saturation of the amplifier, a detected signal level would be reduced, thus causing a problem that sensitivity in light reception and detection accuracy of the photo-plethysmographic signal would degrade.

Moreover, conversion to the digital signal by the AD converter is required to execute the signal processing in the processor, etc. On that occasion, if the noise component attributable to the extraneous light is superimposed on the electrical signal from the light receiver, the electrical signal including the noise component is coded and, therefore, resolution of the AD converter has to be sufficiently increased with respect to a detection signal. For that reason, a dynamic range including the noise component as well needs to be prepared, thus causing another problem of raising the manufacturing cost.

On the other hand, Patent Document 2 discloses the technique of, after separating the signal from the detection element into the DC component and the AC component and amplifying them, converting each of those components to the digital signal by the AD converter. In the disclosed technique, however, the DC component and the AC component are separately subjected to signal processing, and an amplitude ratio between the DC component and the AC component is not restored to the same ratio as that when the signal has been output from the detection element. Accordingly, the converted digital signals cannot be directly applied to, for example, the case where the AC component is normalized using the DC component. In addition, in the optical sensor device disclosed in Patent Document 2, because the DC component and the AC component are detected in synchronism, the DC component and the AC component have to be converted to the respective digital signals by separate AD converters. Hence the manufacturing cost tends to increase.

SUMMARY OF THE INVENTION

The present invention has been accomplished in view of the problems described above, and an object of the present invention is to provide an optical sensor device, which can reduce the cost, and which allows an AC component to be normalized using a DC component.

(1) Accordingly, the present invention provides an optical sensor device comprising a light emitter for emitting light that blinks at a predetermined frequency set in advance, and outputting the light toward a measurement target, a light receiver for receiving the light emitted from the light emitter and reflected by or transmitted through the measurement target, and outputting an electrical signal obtained with photoelectric conversion of the received light, a filter circuit having, as a pass band, a band that corresponds to a part of the electrical signal output from the light receiver and that includes the predetermined frequency of the light emitter, and outputting a modulation signal modulated at the predetermined frequency of the light emitter, an amplifier for amplifying the modulation signal output from the filter circuit, an AD converter for converting the modulation signal, which is an analog signal after being amplified by the amplifier, to a digital signal, and an arithmetic processing unit for calculating a DC component and an AC component of the electrical signal based on the digital signal output from the AD converter.

According to the present invention, the light emitter emits the light at the predetermined frequency set in advance, and the filter circuit outputs the modulation signal, which is contained in the electrical signal output from the light receiver and which is modulated at the predetermined frequency of the light emitter. The modulation signal contains a DC component attributable to the light reflected by or transmitted through the measurement target, and an AC component corresponding to temporal changes in absorbance of the measurement target. The modulation signal is converted to a digital signal by the AD converter. Therefore, the arithmetic processing unit can calculate the DC component and the AC component of the electrical signal, which is output from the light receiver, based on the modulation signal obtained as the digital signal. More specifically, for example, the arithmetic processing unit can calculate the DC component of the electrical signal by taking a time-average value of the modulation signal, and the AC component of the electrical signal by subtracting the DC component from the modulation signal. Hence the AC component can be normalized by employing the calculated DC component.

Furthermore, since the filter circuit can cut off signals of lower frequencies than the predetermined frequency, a cutoff frequency of the filter circuit can be increased to a value near the predetermined frequency of the light emitter. Accordingly, capacitance, for example, used in the filter circuit can be reduced, and reduction in size and cost can be realized.

Moreover, since the modulation signal output from the filter circuit is amplified by the amplifier, the modulation signal can be amplified up to a range near the amplitude range of the AD converter without being affected by signals of lower frequencies than the predetermined frequency of the light emitter, whereby a signal to noise ratio (S/N) can be stably ensured at a satisfactory level. In addition, since an amplitude range of the modulation signal input to the AD converter is stabilized, resolution per bit of the AD converter is widened. As a result, a bit width of the AD converter can be reduced, and the cost can also be reduced.

(2) In the present invention, the light emitter includes two light emitting elements emitting lights in first and second wavelength bands different from each other, the light receiver outputs first and second electrical signals corresponding respectively to the lights in first and second wavelength bands, and the arithmetic processing unit includes absorbance ratio calculation means for calculating an absorbance ratio of the measurement target based on a ratio of a first ratio between an amplitude of a first AC component and a first DC component, both obtained from the first electrical signal, to a second ratio between an amplitude of a second AC component and a second DC component, both obtained from the second electrical signal.

According to the present invention, since the light emitter includes two light emitting elements outputting the lights in first and second wavelength bands, and the light receiver outputs the first and second electrical signals corresponding respectively to the lights in first and second wavelength bands, the absorbance ratio calculation means in the arithmetic processing unit can calculate the absorbance ratio of the measurement target based on the ratio of the first ratio between the amplitude of the first AC component and the first DC component, both obtained from the first electrical signal, to the second ratio between the amplitude of the second AC component and the second DC component, both obtained from the second electrical signal. As a result, even when the light emission intensity of the light emitter and the light reception sensitivity of the light receiver are different between the first and second wavelength bands, the resultant influence can be reduced.

(3) In the present invention, the arithmetic processing unit includes DC component calculation means for calculating the DC component of the electrical signal by taking a time-average value of the modulation signal, and AC component calculation means for calculating the AC component of the electrical signals by excluding the DC component, which has been calculated by the DC component calculation means, from the modulation signal.

According to the present invention, the DC component calculation means in the arithmetic processing unit can calculate the DC component of the electrical signal by taking the time-average value of the modulation signal. Moreover, the AC component calculation means in the arithmetic processing unit can calculate the AC component of the electrical signal by excluding the DC component, which has been calculated by the DC component calculation means, from the modulation signal.

(4) In the present invention, the DC component calculation means is constituted by total component calculation means for calculating a total DC component based on both extraneous light noise and the light from the light emitter by employing a signal that is contained in the modulation signal and that is obtained during a light emission on-period of the light emitter, noise component calculation means for calculating a DC component attributable to the extraneous light noise by employing a signal that is contained in the modulation signal and that is obtained during a light emission off-period of the light emitter, and noise excluded component calculation means for calculating a DC component attributable to the light from the light emitter by excluding the DC component, which has been calculated by the noise component calculation means, from the DC component having been calculated by the total component calculation means.

According to the present invention, the total component calculation means in the DC component calculation means can calculate the total DC component based on both extraneous light noise and the light from the light emitter by employing a signal that is contained in the modulation signal and that is obtained during a light emission on-period of the light emitter. The noise component calculation means in the DC component calculation means can calculate the DC component attributable to the extraneous light noise by employing the signal that is contained in the modulation signal and that is obtained during a light emission off-period of the light emitter. The noise excluded component calculation means in the DC component calculation means can calculate the DC component attributable to the light from the light emitter by excluding the DC component, which has been calculated by the noise component calculation means, from the DC component having been calculated by the total component calculation means. As a result, the arithmetic processing unit can normalize the AC component by employing the DC component from which the influence of the extraneous light noise has been excluded, whereby the absorbance ratio can be obtained with higher accuracy.

(5) In the present invention, the optical sensor device further comprises a separation circuit including the filter circuit and separating the modulation signal and the DC component of the electrical signal, the AD converter converts, in addition to the modulation signal, the DC component of the electrical signal, which has been separated by the separation circuit, to a digital signal, and the arithmetic processing unit converts the modulation signal and the DC component of the electrical signal in accordance with an amplification factor of the amplifier such that an amplitude ratio between the modulation signal and the DC component of the electrical signal, both output as the digital signals from the AD converter, comes back to a state before the amplification by the amplifier, and calculates the AC component of the electrical signal based on the modulation signal obtained as the digital signal.

According to the present invention, since the electrical signal output from the light receiver is separated into the modulation signal containing the AC component and the DC component by the separation circuit, the modulation signal can be amplified by the amplifier separately from the DC component of the electrical signal. The extraneous light noise is mainly superimposed on the DC component, and it is hardly superimposed on the modulation signal containing the AC component. Therefore, a degree of amplification for the modulation signal can be sufficiently increased with respect to the signal range of the AD converter that is a component of a digital processing unit. As a result, the signal to noise ratio (S/N) can be improved and stabilized.

Moreover, since the arithmetic processing unit converts the modulation signal and the DC component of the electrical signal, which are obtained as the digital signals, such that their amplitudes take the same ratio as that before the amplification by the amplifier, it is possible to restore the amplitude ratio between the DC component of the electrical signal and the modulation signal in the state just output from the light receiver. In addition, since the AC component of the electrical signal is calculated based on the modulation signal obtained as the digital signal, the AC component can be normalized by employing the DC component and the AC component after being restored.

(6) In the present invention, the arithmetic processing unit includes noise component calculation means for calculating the DC component attributable to the extraneous light noise based on a signal that is contained in the DC component of the electrical signal and that is obtained during a light emission off-period of the light emitter.

Here, the DC component of the electrical signal having been separated by the separation circuit contains components attributable to both the extraneous light noise and the light from the light emitter. Since the arithmetic processing unit can calculate the DC component attributable to the extraneous light noise by the noise component calculation means, the DC component attributable to the extraneous light noise can be excluded from the DC component output from the separation circuit. Thus, the AC component can be normalized by employing the DC component from which an influence of the extraneous light noise has been excluded, whereby the absorbance ratio can be determined with higher accuracy.

(7) The present invention further provides an optical sensor device comprising a light emitter for emitting light toward a measurement target, and a light receiver for receiving the light emitted from the light emitter and reflected by or transmitted through the measurement target, and outputting an electrical signal obtained with photoelectric conversion of the received light, wherein the optical sensor device further comprises a separation circuit for separating the electrical signal output from the light receiver into a DC component and an AC component, an amplification circuit for amplifying the DC component and the AC component, which have been separated by the separation circuit, at separate amplification factors, an AD converter for converting the DC component and the AC component, analog signals amplified by the amplification circuit, to digital signals, and an arithmetic processing unit for restoring the DC component and the AC component of the electrical signal by converting the DC component and the AC component output as the digital signals from the AD converter in accordance with the separate amplification factors of the amplification circuit such that an amplitude ratio between the DC component and the AC component output as the digital signals comes back to a state before the amplification by the amplification circuit.

According to the present invention, the electrical signal output from the light receiver is separated into the DC component and the AC component by the separation circuit, and the DC component and the AC component having been separated from each other are amplified at the separate amplification factors by the amplification circuit. Therefore, saturation of the amplification circuit due to the extraneous light noise can be suppressed by reducing the amplification factor of the DC component. On the other hand, the extraneous light noise is mainly superimposed on the DC component, and it is hardly superimposed on the AC component. Therefore, a degree of amplification for the AC component can be sufficiently increased with respect to the signal range of the AD converter that is a component of the digital processing unit. As a result, the signal to noise ratio (S/N) can be improved and stabilized.

Moreover, since the DC component and the AC component can be both amplified up to a range near the amplitude range of the AD converter, a signal to noise ratio (S/N) can be stably ensured at a satisfactory level for each of the DC component and the AC component. In addition, since an amplitude range of the signal input to the AD converter is stabilized, resolution per bit of the AD converter is widened. As a result, a bit width of the AD converter can be reduced, and the cost can also be reduced.

Furthermore, since the arithmetic processing unit converts the DC component and the AC component, which are obtained as the digital signals, such that their amplitudes take the same ratio as that before the amplification by the amplification circuit, it is possible to restore the amplitude ratio between the DC component and the AC component of the electrical signal in the state just output from the light receiver. Accordingly, the AC component can be normalized, for example, by employing the DC component and the AC component after being restored.

In the present invention, the light emitter may be configured to emit light blinking at a predetermined frequency set in advance. The separation circuit may be configured to have, as a pass band, a band including the predetermined frequency of the light emitter, and to output the AC component modulated at the predetermined frequency of the light emitter

DETAILED DESCRIPTION OF THE EXEMPLARY EMBODIMENTS

Optical sensor devices according to embodiments of the present invention will be described in detail below with reference to the accompanying drawings.

Figure 1:
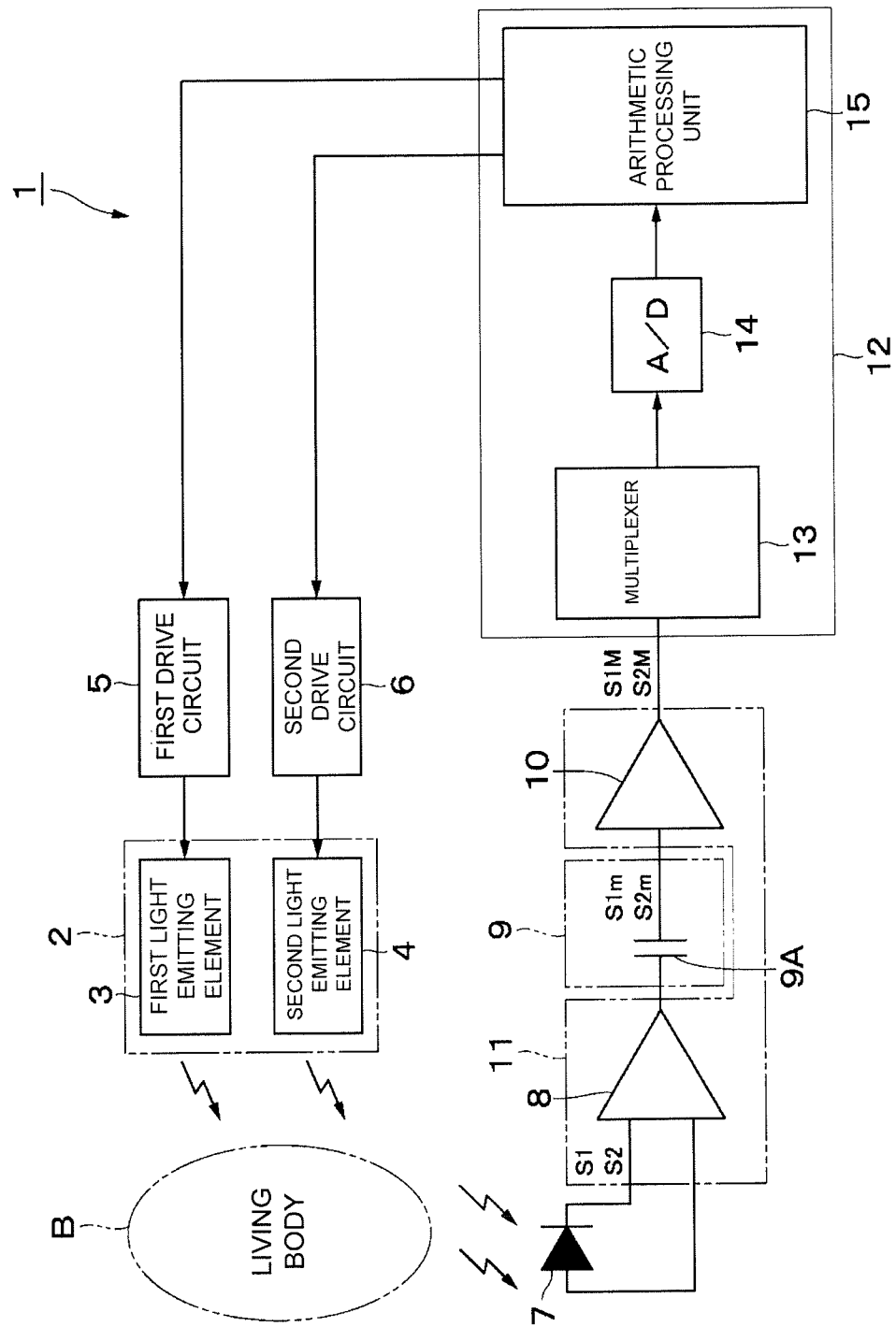
FIG. 1 is an overall block diagram of an optical sensor device according to a first embodiment.

FIG. 1 illustrates an optical sensor device 1 according to a first embodiment. The optical sensor device 1 detects, for example, a photo-plethysmographic signal (pulse wave signal) corresponding to the pulse of a living body B that is a measurement target.

A light emitter 2 is constituted by first and second light emitting elements 3 and 4 that output lights in first and second wavelength bands different from each other, respectively. The first and second light emitting elements 3 and 4 are each constituted by, e.g., a light emitting diode (LED). Herein, the first light emitting element 3 emits, e.g., red light in a band of 700 nm, and the second light emitting element 4 emits, e.g., infrared light in a band of 900 nm.

First and second drive circuits 5 and 6 are connected to the first and second light emitting elements 3 and 4, respectively. The first and second light emitting elements 3 and 4 emit lights blinking in accordance with drive currents supplied from the first and second drive circuits 5 and 6, respectively.

Herein, the first drive circuit 5 supplies a drive current that is pulse-modulated at a predetermined frequency f set in advance. The predetermined frequency f is set to a frequency higher than a signal frequency (e.g., about several Hz) of the photo-plethysmographic signal. Preferably, the predetermined frequency f is set to a value (e.g., about several hundreds Hz) higher than the signal frequency of the photo-plethysmographic signal by ten or more times within a range in which a processing circuit 12 is able to execute processing. In addition, the predetermined frequency f is set to a value (e.g., f=100 Hz) sufficiently lower than the changeover cycle (e.g., 400 Hz) of an AD converter 14 such that conversion to a digital signal can be performed by the AD converter 14.

The second drive circuit 6 also has substantially the same configuration as that of the first drive circuit 5. Thus, the second drive circuit 6 supplies a drive current, which is pulse-modulated at the same predetermined frequency f as that in the first drive circuit 5, to the second light emitting element 4, thereby causing the second light emitting element 4 to emit blinking light. On that occasion, for example, the first and second light emitting elements 3 and 4 alternately emit the lights at timings different from each other.

However, when a light receiver 7 can separately receive the lights in the first and second wavelength bands, the first and second light emitting elements 3 and 4 may be configured to emit the lights at the same timing in synchronism. The first and second light emitting elements 3 and 4 may be each constituted using a vertical cavity surface emitting laser (VCSEL) or a laser diode (LD).

The light receiver 7 is constituted by, e.g., a light receiving element, such as a photodiode (PD). The light receiver 7 receives an optical signal and outputs it after photoelectric conversion to an electrical signal, e.g., a current signal or a voltage signal. More specifically, the light receiver 7 receives the lights emitted from the light emitting elements 3 and 4 and reflected by or transmitted through the living body B, converts the received lights to first and second detection signals S1 and S2 in the form of electrical signals, and outputs the detection signals S1 and S2 to a preamplifier 8. Here, the first detection signal S1 is a signal corresponding to the light in the first wavelength band, and the second detection signal S2 is a signal corresponding to the light in the second wavelength band.

The light receiving element constituting the light receiver 7 may be a phototransistor, as another example. The light receiver 7 may be constituted using a single light receiving element, or using a plurality of light receiving elements, which receive lights in different wavelength bands by employing optical filters, for example.

The preamplifier 8 is constituted using, e.g., an operational amplifier. An input terminal of the preamplifier 8 is connected to the light receiver 7. The preamplifier 8 amplifies the detection signals S1 and S2, output from the light receiver 7, at an amplification factor Gx and outputs the amplified signals to a filter circuit 9.

The filter circuit 9 is constituted by a capacitor 9A, which serves as a coupling capacitor connected between the preamplifier 8 and a post-amplifier 10. The filter circuit 9 functions as a high-pass filter allowing passage of signals of frequencies, equal to or higher than the predetermined frequency f at which the first and second light emitting elements 3 and 4 emit the blinking lights. The cutoff frequency of the filter circuit 9 is set to a value as high as possible within a range allowing the signals of the predetermined frequency f to pass there through.

Because the light emitter 2 emits the lights blinking at the predetermined frequency f, the first and second detection signals S1 and S2 are each a signal obtained with amplitude modulation of the signal of the predetermined frequency f. On that occasion, because the capacitor 9A cuts off signals of lower frequencies than the predetermined frequency f, the filter circuit 9 outputs modulation signals S1m and S2m that are obtained respectively from the first and second detection signals S1 and S2 through amplitude modulation at the predetermined frequency f.

The post-amplifier 10 is an amplifier for amplifying the modulation signals S1m and S2m. The post-amplifier 10 is constituted using an operational amplifier, for example, and it constitutes an amplification circuit 11 in combination with the preamplifier 8. The post-amplifier 10 is connected to the output side of the filter circuit 9. The post-amplifier 10 amplifies the first and second modulation signals S1m and S2m at an amplification factor Gy, and then outputs first and second modulation signals S1M and S2M after the amplification. Here, an amplification factor Gm of the first and second modulation signals S1M and S2M is set by both the preamplifier 8 and the post-amplifier 10, and the amplification factor Gm is equal to the product of the amplification factor Gx and the amplification factor Gy (i.e., Gm=Gx×Gy). Thus, the amplification factors Gx and Gy of the preamplifier 8 and the post-amplifier 10 are set such that an amplitude range of each of the first and second modulation signals S1M and S2M has a value comparable to that of an input range of the AD converter 14.

The processing circuit 12 is mainly constituted by a multiplexer 13, an AD converter 14, and an arithmetic processing unit 15.

The multiplexer 13 connects the post-amplifier 10 to the AD converter 14. Accordingly, the first and second modulation signals S1M and S2M output from the post-amplifier 10 are input to the AD converter 14 through the multiplexer 13. For example, when the first and second light emitting elements 3 and 4 are driven to emit the lights alternately, the first and second modulation signals S1M and S2M can be input, as a series of time-divided signals, to the AD converter 14 in the form of a single unit. In such a case, the post-amplifier 10 may be directly connected to the AD converter 14 by omitting the multiplexer 13.

The AD converter 14 converts the first and second modulation signals S1M and S2M from analog signals to digital signals. At that time, the AD converter 14 converts, for example, only plus-side values of the first and second modulation signals S1M and S2M to digital signals. Moreover, the first and second modulation signals S1M and S2M are set by the preamplifier 8 and the post-amplifier 10 to values comparable to the input range of the AD converter 14. Therefore, the AD converter 14 can convert the first and second modulation signals S1M and S2M to the digital signals by employing the entire input range thereof.

The arithmetic processing unit 15 is constituted by a microcomputer, for example. By executing a processing program illustrated in FIG. 2, the arithmetic processing unit 15 calculates respective DC components S1d and S2d and respective AC components S1a and S2a of the first and second detection signals S1 and S2 based on the first and second modulation signals S1M and S2M output from the AD converter 14, and further determines an absorbance ratio R12 of the living body B. The processing program illustrated in FIG. 2 is executed, for example, each time the first and second modulation signals S1M and S2M are updated by the AD converter 14.

Figure 2:
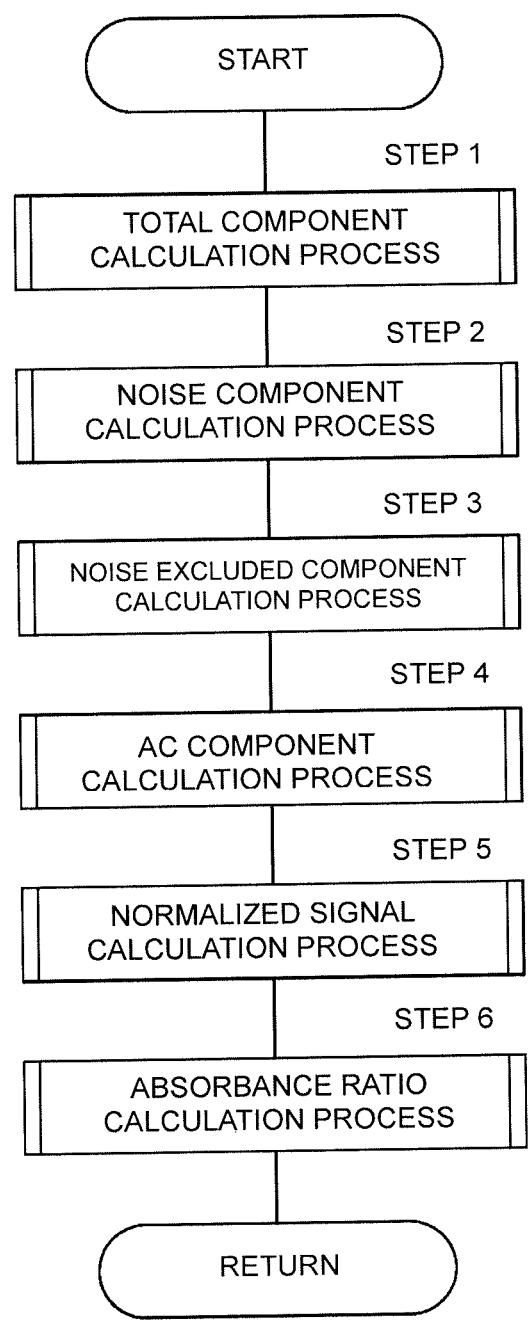
FIG. 2 is a flowchart of a processing program executed by an arithmetic processing unit in FIG. 1.

In more detail, the arithmetic processing unit 15 executes a DC component calculation process illustrated in steps 1 to 3 of FIG. 2, and calculates the respective DC components S1d and S2d a of the first and second detection signals S1 and S2 based on the first and second modulation signals S1M and S2M.

The first and second modulation signals S1M and S2M contain DC components, which are attributable to extraneous light noise, in addition to the DC components of the lights emitted from the light emitting elements 3 and 4 and reflected by or transmitted through the living body B. In view of the above-mentioned point, in a total component calculation process illustrated in step 1, DC components S1don and S2don attributable to both the extraneous light noise and the lights from the light emitting elements 3 and 4 are calculated by extracting, from the first and second modulation signals S1M and S2M, signals obtained during light emission on-periods of the light emitting elements 3 and 4, and by calculating respective time-average values of the extracted signals. At that time, each time-average value is calculated for a time corresponding to at least one cycle (e.g., about 1 sec) of the photo-plethysmographic signal, preferably two or more cycles, but the time is as short as possible within such a condition.

Next, in a noise component calculation process illustrated in step 2, DC components S1doff and S2doff attributable to the extraneous light noise are calculated by extracting, from the first and second modulation signals S1M and S2M, signals obtained during light emission off-periods of the light emitting elements 3 and 4, and by calculating respective time-average values of the extracted signals.

Next, in a noise excluded component calculation process illustrated in step 3, the DC components S1d and S2d attributable to the lights from the light emitter 2 are calculated by excluding the DC components S1doff and S2doff, calculated in step 2, from the DC components S1don and S2don calculated in step 1, respectively.

Next, in an AC component calculation process illustrated in step 4, the AC components S1a and S2a are calculated by extracting, from the first and second modulation signals S1M and S2M, signals obtained during light emission on-periods of the light emitting elements 3 and 4, and by subtracting the DC components S1don and S2don, calculated in step 1, from the extracted signals.

Next, in step 5, a normalized signal calculation process is executed to normalize amplitudes ΔS1a and ΔS2a of the AC components S1a and S2a by employing the DC components S1d and S2d, respectively. More specifically, normalized signals S10 and S20 are calculated as first and second ratios by dividing the amplitudes ΔS1a and ΔS2a by the DC components S1d and S2d, respectively, in accordance with the following formula 1.

$$S10 = \frac{\Delta S1a}{S1d}$$ [Math. 1]

$$S20 = \frac{\Delta S2a}{S2d}$$

Next, in step 6, an absorbance ratio calculation process is executed to calculate the absorbance ratio R12 by employing the normalized signals S10 and S20. More specifically, the absorbance ratio R12 is calculated by dividing the normalized signal S10 corresponding to the first wavelength by the normalized signal S20 corresponding to the second wavelength in accordance with the following formula 2.

$$R12 = \frac{S10}{S20}$$ [Math. 2]

The arithmetic processing unit 15 may produce, in addition to the absorbance ratio R12, biological information, such as a degree of oxygen saturation, acceleration pulse wave, and pulse fluctuation, based on the first and second detection signals S1 and S2. Furthermore, the arithmetic processing unit 15 is connected to the first and second drive circuits 5 and 6 to establish synchronism between the light emission by the first and second light emitting elements 3 and 4 and the light reception by the light receiver 7 based on the operations of the first and second drive circuits 5 and 6.

The optical sensor device 1 according to the first embodiment of the present invention is constituted as described above, and the operation of the optical sensor device 1 is described below.

Figure 3:
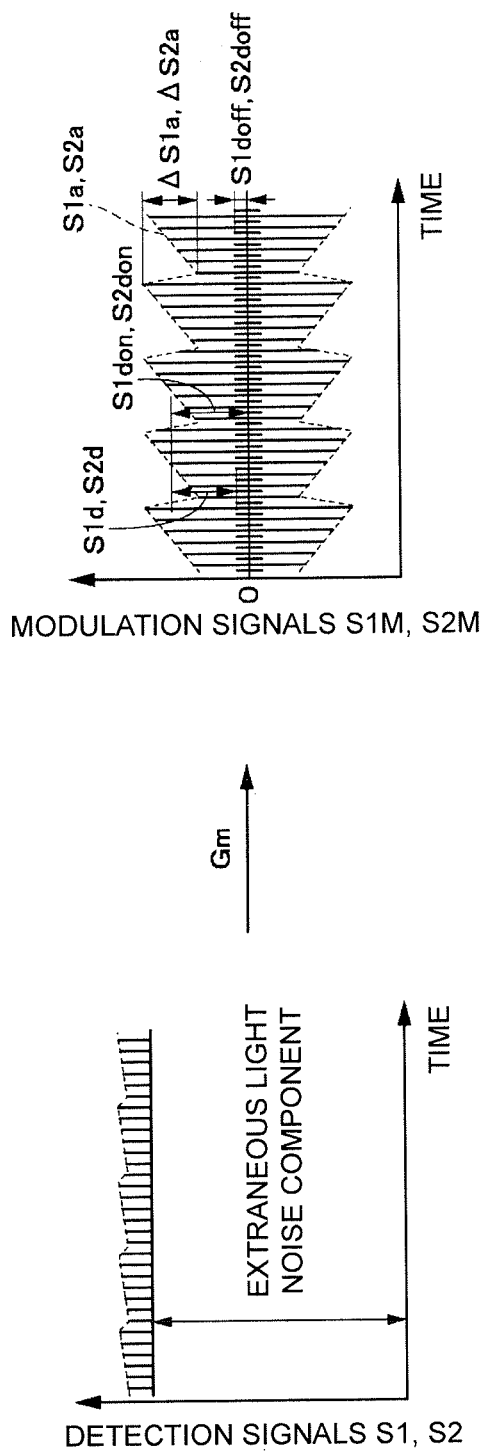
FIG. 3 is an explanatory view illustrating first and second detection signals and modulation signals in the optical sensor device in FIG. 1.

First, a switch (not illustrated) of the optical sensor device 1 is turned on in a state that the light emitter 2 and the light receiver 7 are disposed near the living body B. Upon the turning-on of the switch, the first and second light emitting elements 3 and 4 of the light emitter 2 output the lights in the first and second wavelength bands, respectively. The light receiver 7 receives the emitted lights after being reflected by or transmitted through the living body B, and outputs the first and second detection signals S1 and S2 corresponding to the first and second wavelength bands, respectively. As illustrated in FIG. 3, the modulation signals S1m and S2m are extracted from the first and second detection signals S1 and S2, respectively, by the filter circuit 9 and are input to the processing circuit 12. In the processing circuit 12, the modulation signals S1M and S2M are converted to the digital signals by the AD converter 14, and the DC components S1d and S2d and the AC components S1a and S2a are calculated by the arithmetic processing unit 15. Other various processes are also executed by the arithmetic processing unit 15.

Because the optical sensor device is configured here such that the light emitter 2 emits the lights at the predetermined frequency f and the filter circuit 9 outputs the modulation signals S1m and S2m modulated at the predetermined frequency f of the light emitter 2, the cutoff frequency of the filter circuit 9 can be set to a higher value, and the capacitance of the capacitor 9A can be reduced.

To explain in more detail, the photo-plethysmographic signal is a low-frequency signal of about several Hz corresponding to the pulse of the living body. To separate the photo-plethysmographic signal, therefore, the cutoff frequency is to be set as low as about several Hz, and a capacitor having a large capacity of, e.g., about several hundreds μF is required. In contrast, in the first embodiment, the filter circuit 9 is just required to allow passage of signals of the predetermined frequency f, which is higher than the frequency of the photoplethysmographic signal, in order to separate the modulation signals S1m and S2m modulated at the predetermined frequency f of the light emitter 2. Therefore, the cutoff frequency of the filter circuit 9 can be set to a higher value, and the capacitance of the capacitor 9A can be reduced to be smaller than 1 μF, for example. As a result, miniaturization and cost-reduction can be realized.

Moreover, the modulation signals S1M and S2M resulting from amplifying the modulation signals S1m and S2m contain not only the DC components S2d and S2d attributable to the lights from the light emitting elements 3 and 4, but also the AC components S1a and S2a attributable to the photo-plethysmographic signal. The DC components S2d and S2d can be determined from respective time-average values of the modulation signals S1M and S2M. In the case of taking the time-average values of signals that are contained in the modulation signals S1M and S2M and that are obtained during the light emission on-periods of the light emitting elements 3 and 4, the time-average values include the component attributable to the extraneous light noise in addition to the components corresponding to the lights from the light emitting elements 3 and 4. Accordingly, in the first embodiment, of the modulation signals S1M and S2M, the DC components S1doff and S2doff resulting from time-averaging the signals obtained during the light emission off-periods of the light emitting elements 3 and 4 are subtracted from the DC components S1don and S2don resulting from time-averaging the signals obtained during the light emission on-periods of the light emitting elements 3 and 4, respectively. As a result, the DC components S2d and S2d attributable to the lights from the light emitting elements 3 and 4 can be calculated by excluding the component attributable to the extraneous light noise.

Furthermore, the arithmetic processing unit 15 can calculate the absorbance ratio R12 based on a ratio of the normalized signal S10, which is obtained as a first ratio of the amplitude ΔS1a of a first AC component S1a and a first DC component S1d, to the normalized signal S20, which is obtained as a second ratio of the amplitude ΔS2a of a second AC component S2a and a second DC component S2d. As a result, even when the light emission intensity of the light emitter 2 and the light reception sensitivity of the light receiver 7 are different between the first and second wavelength bands, the resultant influence can be reduced. In addition, since the amplitudes ΔS1a and ΔS2a of the AC components S1a and S2a are normalized by employing the DC components S1d and S2d obtained after removing the influence of the extraneous light noise, the absorbance ratio R12 of the living body B can be determined with high accuracy.

The modulation signals S1M and S2M are signals amplified at the amplification factor Gm by the preamplifier 8 and the post-amplifier 10. On that occasion, since a DC noise component, etc., excluded from the modulation signals S1M and S2M by the filter circuit 9, they undergo a smaller influence of the extraneous light noise than the first and second detection signals S1 and S2. Therefore, saturation of both the amplifiers 8 and 10 caused by the extraneous light noise can be suppressed. Moreover, since respective amplitude ranges of the modulation signals S1m and S2m are stabilized, respective amplitude ranges of the modulation signals S1M and S2M after the amplification can be each set to a value comparable to that of the input range of the AD converter 14. Accordingly, a signal to noise ratio (S/N) can be stably ensured at a satisfactory level. In addition, since minimum resolution representing resolution per the least significant bit of the AD converter 14 is improved, a bit width of the AD converter 14 can be reduced, and the cost can also be reduced.

In the first embodiment described above, steps 1 to 3 in FIG. 2 represent a practical example of DC component calculation means. Step 1 in FIG. 2 represents a practical example of total component calculation means. Step 2 in FIG. 2 represents a practical example of noise component calculation means. Step 3 in FIG. 2 represents a practical example of noise excluded component calculation means. Step 4 in FIG. 2 represents a practical example of AC component calculation means. Step 6 in FIG. 2 represents a practical example of absorbance ratio calculation means.

Figure 4:
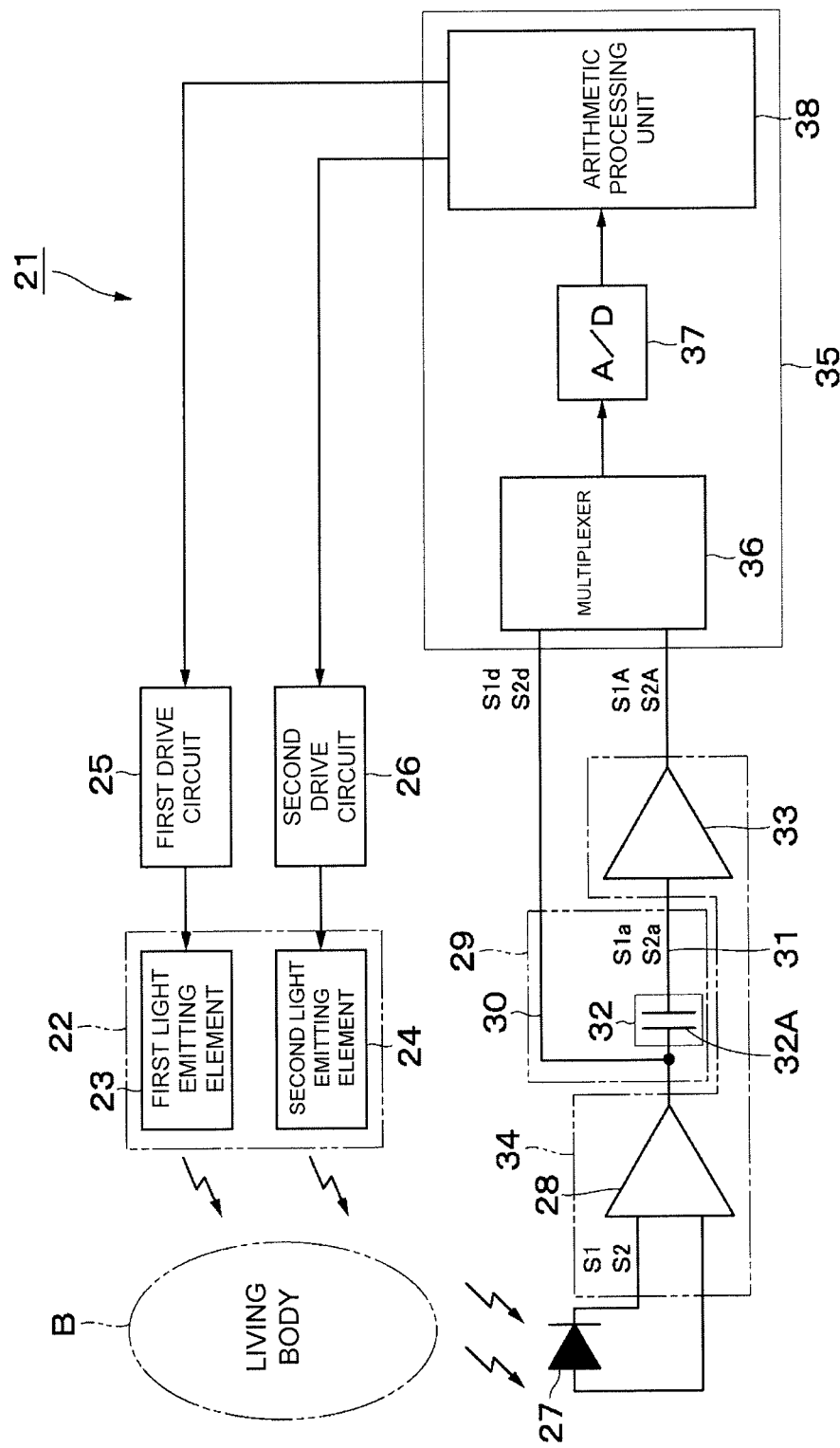
FIG. 4 is an overall block diagram of an optical sensor device according to a second embodiment.

FIG. 4 illustrates an optical sensor device 21 according to a second embodiment. The optical sensor device 21 detects, for example, a photo-plethysmographic signal (pulse wave signal) corresponding to the pulse of a living body B as a measurement target.

A light emitter 22 is constituted by first and second light emitting elements 23 and 24 that output lights in first and second wavelength bands different from each other, respectively. The first and second light emitting elements 23 and 24 are each constituted by, e.g., a light emitting diode (LED). Herein, the first light emitting element 23 emits, e.g., red light in a band of 700 nm, and the second light emitting element 24 emits, e.g., infrared light in a band of 900 nm.

First and second drive circuits 25 and 26 are connected to the first and second light emitting elements 23 and 24, respectively. The first and second light emitting elements 23 and 24 emit continuously lasting lights or intermittently blanking lights in accordance with drive currents supplied from the first and second drive circuits 25 and 26, respectively.

Herein, the first and second light emitting elements 23 and 24 may alternately emit the lights in a time-division manner, for example. Alternatively, when a light receiver 27 can separately receive the lights in the first and second wavelength bands, the first and second light emitting elements 23 and 24 may emit the lights at the same timing in synchronism. The first and second light emitting elements 23 and 24 may be each constituted using a vertical cavity surface emitting laser (VCSEL) or a laser diode (LD).

The light receiver 27 is constituted by, e.g., a light receiving element, such as a photodiode (PD). The light receiver 27 receives an optical signal and outputs it after photoelectric conversion to an electrical signal, e.g., a current signal or a voltage signal. More specifically, the light receiver 27 receives the lights emitted from the light emitting elements 23 and 24 and reflected by or transmitted through the living body B, converts the received lights to first and second detection signals S1 and S2 in the form of electrical signals, and outputs the detection signals S1 and S2 to a preamplifier 28. Here, the first detection signal S1 is a signal corresponding to the light in the first wavelength band, and the second detection signal S2 is a signal corresponding to the light in the second wavelength band.

The light receiving element constituting the light receiver 27 may be a phototransistor, as another example. The light receiver 27 may be constituted using a single light receiving element, or using a plurality of light receiving elements, which receive lights in different wavelength bands by employing optical filters, for example.

The preamplifier 28 is constituted using, e.g., an operational amplifier. An input terminal of the preamplifier 28 is connected to the light receiver 27. The preamplifier 28 amplifies the detection signals S1 and S2, output from the light receiver 27, at an amplification factor Gx and outputs the amplified signals to a separation circuit 29.

The separation circuit 29 is constituted by first and second branch lines 30 and 31, which are connected in parallel to an output terminal of the preamplifier 28, and by a filter circuit 32, which functions as a high-pass filter connected to an intermediate point of the second branch line 31. The filter circuit 32 is constituted by a capacitor 32A that serves as a coupling capacitor connected between the preamplifier 28 and a post-amplifier 33.

The first branch line 30 transmits the first and second detection signals S1 and S2 output from the preamplifier 28, as they are, including the DC components S1d and S2d. Therefore, the first branch line 30 serves as a DC component transmission path for transmitting the DC components S1d and S2d of the first and second detection signals S1 and S2.

On the other hand, the capacitor 32A functioning as a coupling capacitor is disposed in the second branch line 31. Because the DC components S1d and S2d of the first and second detection signals S1 and S2 are blocked by the capacitor 32A, the second branch line 31 serves as an AC component transmission path for transmitting the AC components S1a and S2a of the first and second detection signals S1 and S2. The capacitance of the capacitor 32A is set depending on frequencies of the AC components S1a and S2a of the first and second detection signals S1 and S2, which are to be passed through the capacitor 32A.

When the first and second AC components S1a and S2a are sufficiently smaller (e.g., 1/10 or less) than the first and second DC components S1d and S2d, the first and second detection signals S1 and S2 become substantially the same signals as the DC components S1d and S2d, respectively. Therefore, the first branch line 30 transmits the first and second detection signals S1 and S2 as they are. On the contrary, when the first and second AC components S1a and S2a are comparable to the first and second DC components S1d and S2d, or when the first and second AC components S1a and S2a are larger than the first and second DC components S1d and S2d, a low-pass filter, e.g., an integrator, may be connected to the first branch line 30.

The post-amplifier 33 is an amplifier for amplifying the first and second AC components S1a and S2a. The post-amplifier 33 is connected to the second branch line 31 on the output side of the capacitor 32A. The post-amplifier 33 amplifies the first and second AC components S1a and S2a of the first and second detection signals S1 and S2 at an amplification factor Gy, and then outputs first and second AC components S1A and S2A after the amplification. The post-amplifier 33 is constituted using an operational amplifier, for example, and it constitutes an amplification circuit 34 in combination with the preamplifier 28. Here, an amplification factor Gd of the first and second DC components S1d and S2d of the first and second detection signals S1 and S2 is set by the preamplifier 28, and the amplification factor Gd is equal to the amplification factor Gx (i.e., Gd=Gx). On the other hand, an amplification factor Ga of the first and second AC components S1A and S2A of the first and second detection signals S1 and S2 is set by both the preamplifier 28 and the post-amplifier 33, and the amplification factor Ga is equal to the product of the amplification factor Gx and the amplification factor Gy (i.e., Ga=Gx×Gy). Thus, the amplification circuit 34 amplifies the DC components S1d and S2d and the AC components S1a and S2a of the first and second detection signals S1 and S2, which are separated by the separation circuit 29, at the separate amplification factors Gd and Ga, respectively.

When the AC components S1a and S2a of the first and second detection signals S1 and S2 are photo-plethysmographic signals, the AC components S1a and S2a changing depending on the blood flow in the living body B are smaller than the DC components S1d and S2d corresponding to the reflected or transmitted lights directly obtained from the living body B. In the amplification circuit 34, therefore, the amplification factor Ga for the AC components S1a and S2a is set to be larger than the amplification factor Gd for the DC components S1d and S2d such that the amplitudes of those components are set to values comparable to the amplitude range of an AD converter 37 described below.

The processing circuit 35 is mainly constituted by a multiplexer 36, the AD converter 37, and an arithmetic processing unit 38.

The multiplexer 36 is connectable to the first branch line 30 of the separation circuit 29, and to the second branch line 31 thereof at a downstream position of the post-amplifier 33. The multiplexer 36 alternately connects the first and second branch lines 30 and 31 to the AD converter 37 in a time-division manner, for example.

When the multiplexer 36 is connected to the first branch line 30, the AD converter 37 converts the DC components S1d and S2d of the first and second detection signals S1 and S2 from analog signals to digital signals, and when the multiplexer 36 is connected to the second branch line 31, the AD converter 37 converts the AC components S1A and S2A of the first and second detection signals S1 and S2 from analog signals to digital signals. At that time, the DC components S1d and S2d and the AC components S1A and S2A of the first and second detection signals S1 and S2 are each set by the amplification circuit 34 to a value comparable to the input range of the AD converter 37. Therefore, the AD converter 37 can convert the DC components S1d and S2d and the AC components S1A and S2A to the digital signals by employing the entire input range thereof.

The first and second detection signals S1 and S2 are directly input, as the DC components S1d and S2d, to the AD converter 37. When the AC components S1a and S2a are sufficiently smaller (e.g., 1/10 or less) than the DC components S1d and S2d and are comparable to the resolution of the AD converter 37, the AC components S1a and S2a are removed when the DC components S1d and S2d are converted to the digital signals by the AD converter 37. On the other hand, when the AC components S1a and S2a are so large as not negligible, it is preferable to previously remove the AC components S1a and S2a contained in the DC components S1d and S2d by employing a low-pass filter, or to determine time-average values of the DC components S1d and S2d having been converted to the digital signals.

The arithmetic processing unit 38 is constituted by a microcomputer, for example. By executing a processing program illustrated in FIG. 5, the arithmetic processing unit 38 restores the first and second detection signals S1 and S2 before the amplification based on the DC components S1d and S2d and the AC components S1A and S2A, which are output from the AD converter 37, and further determines an absorbance ratio R12 of the living body B. The processing program illustrated in FIG. 5 is executed, for example, each time the digital signals of the DC components S1d and S2d and the AC components S1A and S2A are updated by the AD converter 37.

Figure 5:
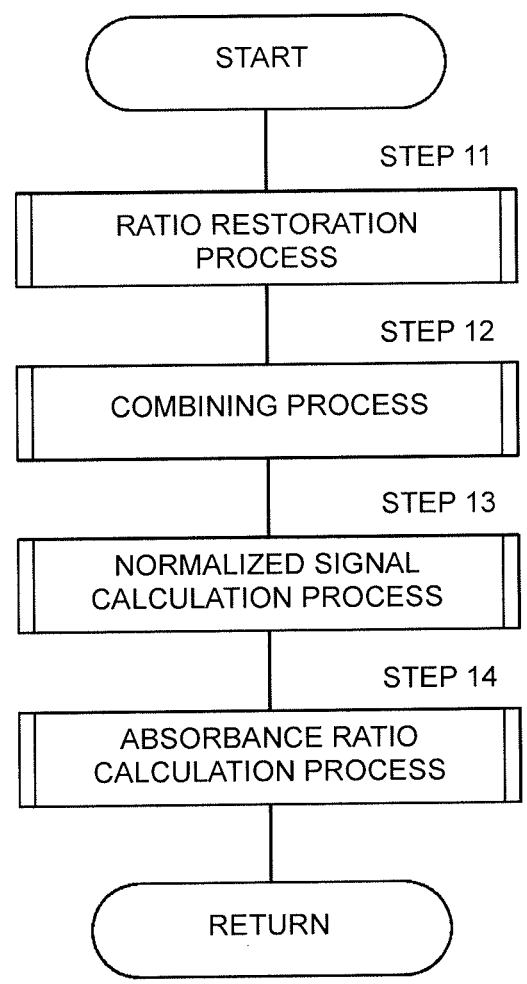
FIG. 5 is a flowchart of a processing program executed by an arithmetic processing unit in FIG. 4.

In more detail, the arithmetic processing unit 38 executes a ratio restoration process, illustrated in step 11 of FIG. 5, by converting the DC components S1d and S2d and the AC components S1A and S2A of the first and second detection signals S1 and S2 based on the amplification factors Gd and Ga such that respective amplitudes of those components are restored to have the same ratios as those before the amplification by the amplification circuit 34. On that occasion, the amplification factors Gd and Ga are different from each other by the amplification factor Gy of the post-amplifier 33, and the amplitudes of the AC components S1A and S2A input to the arithmetic processing unit 38 are larger in amplitude than that of the DC components S1d and S2d by the amplification factor Gy of the post-amplifier 33. In view of such a difference, the arithmetic processing unit 38 calculates restored AC components S1ar and S2ar by dividing the AC components S1A and S2A by the amplification factor Gy as expressed in the following formula 3. As a result, the DC components S1d and S2d and the AC components S1ar and S2ar are restored to have the ratios between their amplitudes (i.e., the amplitude ratios) before the amplification.

$$S1ar = \frac{S1A}{Gy}$$
$$S2ar = \frac{S2A}{Gy}$$

[Math. 3]

Next, in step 12, a combining process of combining the restored AC components S1ar and S2ar with the DC components S1d and S2d, respectively, is executed to obtain first and second restoration signals SR1 and SR2 resulting from restoring the first and second detection signals S1 and S2 before the amplification. More specifically, the first and second restoration signals SR1 and SR2 are calculated by adding the restored AC components S1ar and S2ar to the DC components S1d and S2d, respectively, as expressed in the following formula 4.

$$SR1=S1d+S1ar$$

$$SR2=S2d+S2ar$$

[Math. 4]

Next, in step 13, a normalized signal calculation process is executed to normalize respective amplitudes ΔS1ar and ΔS2ar of the AC components S1ar and S2ar by employing the DC components S1d and S2d, respectively. Here, the amplitudes ΔS1ar and ΔS2ar are obtained by restoring respective amplitudes ΔS1A and ΔS2A of the AC components S1A and S2A after the amplification to the states before the amplification, i.e., by dividing the amplitudes ΔS1A and ΔS2A by the amplification factor Gy. Normalized signals S10 and S20 are calculated as the first and second ratios by dividing the amplitudes ΔS1ar and ΔS2ar by the DC components S2d and S2d, respectively, in accordance with the following formula 5.

$$S10 = \frac{\Delta S1ar}{S1d}$$
$$S20 = \frac{\Delta S2ar}{S2d}$$

[Math. 5]

Next, in step 14, an absorbance ratio calculation process is executed to calculate the absorbance ratio R12 by employing the normalized signals S10 and S20. More specifically, the absorbance ratio R12 is calculated by dividing the normalized signal S10 corresponding to the first wavelength by the normalized signal S20 corresponding to the second wavelength in accordance with the above-described formula 2.

The arithmetic processing unit 38 may produce, in addition to the absorbance ratio R12, biological information, such as a degree of oxygen saturation, acceleration pulse wave, and pulse fluctuation, based on the first and second detection signals S1 and S2. Furthermore, the arithmetic processing unit 38 is connected to the first and second drive circuits 25 and 26 to establish synchronism between the light emission by the first and second light emitting elements 23 and 24 and the light reception by the light receiver 27 based on the operations of the first and second drive circuits 25 and 26.

The optical sensor device 21 according to the second embodiment of the present invention is constituted as described above, and the operation of the optical sensor device 21 is described below.

Figure 6:
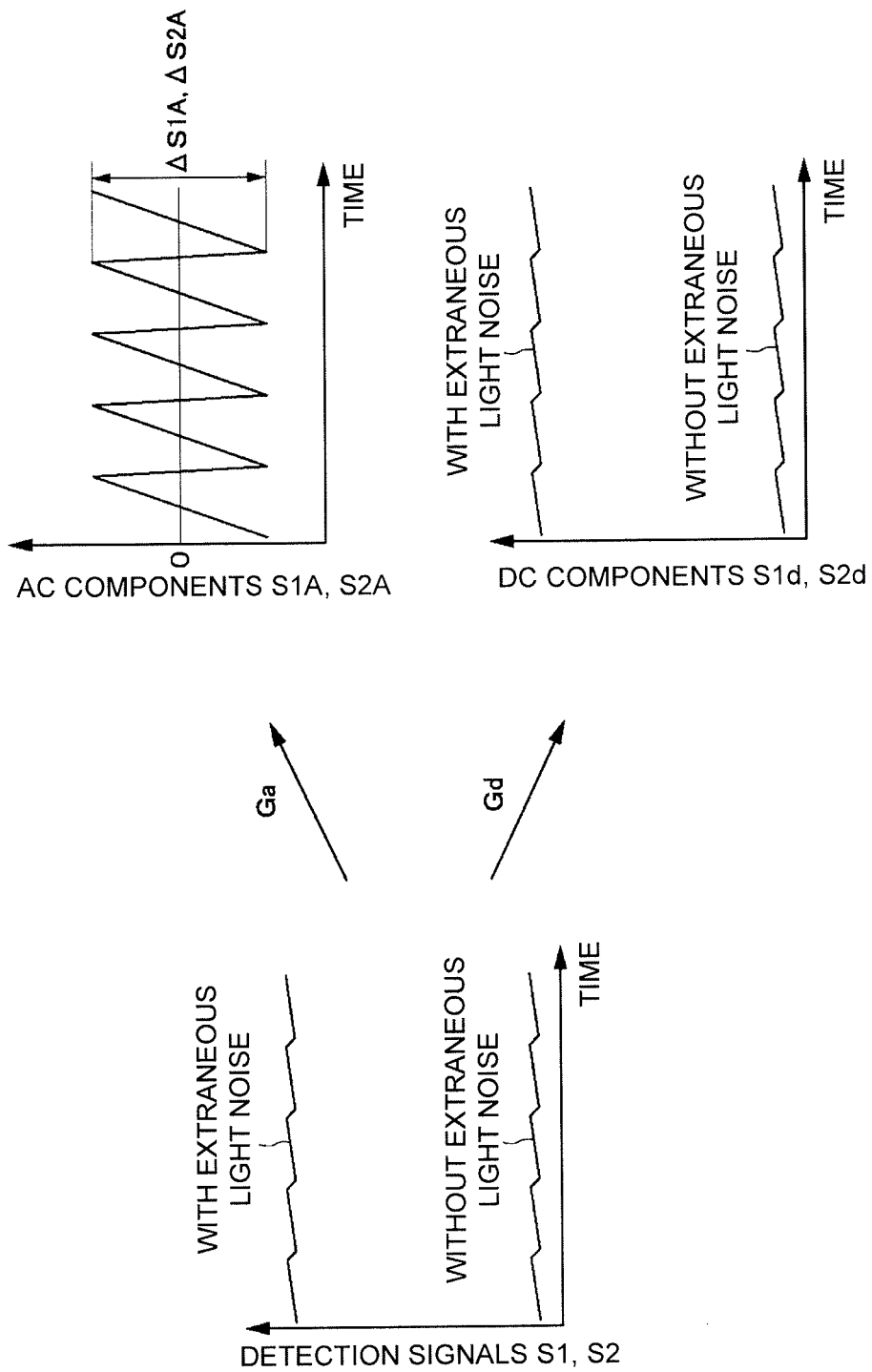
FIG. 6 is an explanatory view illustrating a state where a DC component and an AC component are separated from each of first and second detection signals and are amplified by the optical sensor device in FIG. 4.

First, a switch (not illustrated) of the optical sensor device 21 is turned on in a state that the light emitter 22 and the light receiver 27 are disposed near the living body B. Upon the turning-on of the switch, the first and second light emitting elements 23 and 24 of the light emitter 22 output the lights in the first and second wavelength bands, respectively. The light receiver 27 receives the emitted lights after being reflected by or transmitted through the living body B, and outputs the first and second detection signals S1 and S2 corresponding to the first and second wavelength bands, respectively. The first and second detection signals S1 and S2 are separated by the separation circuit 29 into the DC components S1d and S2d and the AC components S1A and S2A, as illustrated in FIG. 6, which are then input to the processing circuit 35 in the separated state. In the processing circuit 35, the DC components S1d and S2d and the AC components S1A and S2A are converted to the digital signals by the AD converter 37, and various processes are executed by the arithmetic processing unit 38.

Herein, the DC components S1d and S2d and the AC components S1A and S2A are amplified respectively at the separate amplification factors Gd and Ga by the amplification circuit 34. Accordingly, the respective amplitudes of the DC components S1d and S2d and the AC components S1A and S2A can be set to be comparable to each other, and those amplitudes can be set to values comparable to the amplitude range of the AD converter 37. As a result, minimum resolution representing resolution per the least significant bit of the AD converter 37 is improved.

Figure 7:
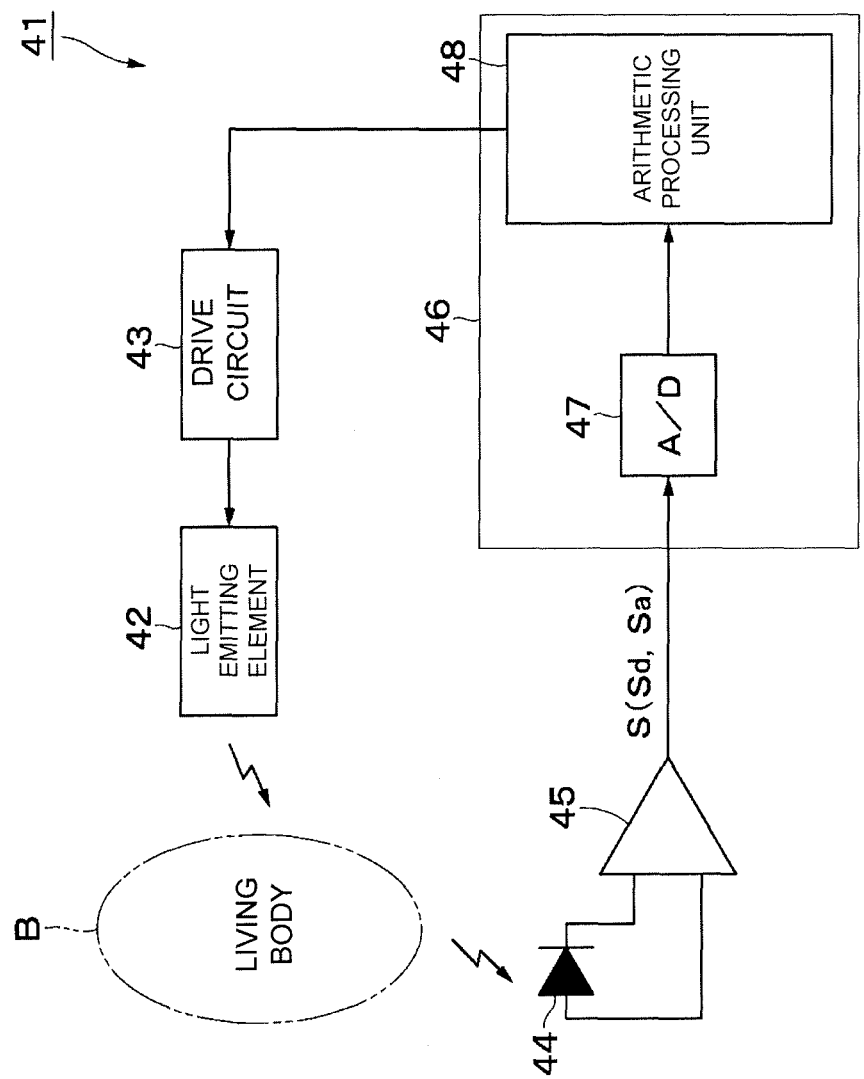
FIG. 7 is an overall block diagram of an optical sensor device according to a comparative example.

The foregoing point is described in more detail with reference to FIG. 7 representing a comparative example. An optical sensor device 41 according to the comparative example, illustrated in FIG. 7, includes a light emitter 42, a drive circuit 43, a light receiver 44, an amplifier 45, and a processing circuit 46. The processing circuit 46 is constituted by an AD converter 47 and an arithmetic processing unit 48. In the optical sensor device 41, a DC component Sd and an AC component Sa of a detection signal S are amplified at the same amplification factor G by the amplifier 45.

It is here assumed that the DC component Sd is 0.01 [V], the AC component Sa is about 1/10 (0.001 [V]) of the DC component Sd, and the DC component Sd is increased about 10 times (i.e., to 0.1 [V]) by the extraneous light noise. In such a case, assuming a maximum voltage level of the AD converter 47 to be 1 [V], the amplification factor G of the amplifier 45 is about 10 at maximum.

Furthermore, an amplitude ratio of the AC component Sa to the DC component Sd is not changed between the input side and the output side of the amplifier 45, the AC component Sa cannot be detected with high accuracy unless the resolution of the AD converter 47 is set to be high. However, the maximum voltage level of the AD converter 47 is determined depending on a maximum value of the DC component Sd attributable to the extraneous light noise. Accordingly, when the resolution of the AD converter 47 is set to 10 bits, minimum resolution is, e.g., about 488 [μV/LSB] for each of the DC component Sd and the AC component Sa.

In contrast, in the optical sensor device 21 according to the second embodiment, the DC components S1d and S2d and the AC components S1A and S2A of the detection signals S1 and S2 are amplified respectively at the separate amplification factors Gd and Ga, for example, by employing the postamplifier 33. Even in the case where the amplitudes of the DC components S1d and S2d and the AC components S1a and S2a and the influence of the extraneous light noise on those amplitudes in the stage before the amplification are the same as in the comparative example described above, therefore, assuming the amplification factor Gd of the DC components S1d and S2d to be 1 and the amplification factor Ga of the AC components S1a and S2a to be 10, both the components can be input to the AD converter 37 with their amplitudes matched to the same value of 0.01 [V]. As a result, even if the DC components S1d and S2d are increased about 10 times (0.1 [V]) by the extraneous light noise, the maximum voltage level of the AD converter 37 can be reduced to 0.1 [V].

In addition, the amplification factor Ga of the AC components S1a and S2a is set to be larger than the amplification factor Gd of the DC components S1d and S2d such that the amplitudes of the AC components S1A and S2A after the amplification come close to the amplitude range of the AD converter 37. Therefore, even when the resolution of the AD converter 37 is reduced to 8 bits, the minimum resolution for the AC components S1A and S2A is increased to, e.g., about 19.53 [μV/LSB]. In this regard, the minimum resolution for the DC components S1d and S2d is, e.g., about 19.53 [μV/LSB] when there is no influence of the extraneous light noise, and is, e.g., about 195.31 [μV/LSB] when there is an influence of the extraneous light noise.

According to the second embodiment, as described above, the minimum resolution of the AD converter 37 can be improved, and an AD converter having lower resolution can be used as the AD converter 37. It is hence possible to reduce the power consumption and the manufacturing cost.

Thus, in the optical sensor device 21 according to the second embodiment, the first and second detection signals S1 and S2 output from the light receiver 27 are separated into the DC components S1d and S2d and the AC components S1a and S2a by the separation circuit 29, and the DC components S1d and S2d and the AC components S1A and S2A, after being separated from each other, are amplified at the separate amplification factors Gd and Ga by the amplification circuit 34, respectively. Therefore, the saturation of the amplification circuit 34 due to the extraneous light noise can be suppressed by reducing the amplification factor Gd of the DC components S1d and S2d. On the other hand, since other signals than the photo-plethysmographic signal are hardly superimposed on the AC components S1a and S2a, the amplification factor Ga for the AC components S1A and S2A can be sufficiently increased with respect to the signal range of the AD converter 37 that is a component of a digital processing unit. As a result, the signal to noise ratio (S/N) can be improved and stabilized.

Furthermore, since the DC components S1d and S2d and the AC components S1A and S2A can be all amplified up to ranges near the amplitude range of the AD converter 37, the signal to noise ratio (S/N) can be stably ensured at a satisfactory level. In addition, since the amplitude range of each signal input to the AD converter 37 is stabilized, voltage resolution of the AD converter 37 per bit is widened. Accordingly, the bit width of the AD converter 37 can be reduced and cost reduction can be realized.

Moreover, since the arithmetic processing unit 38 executes the conversion such that the respective amplitudes of the DC components S1d and S2d and the AC components S1A and S2A of the digital signals take the same ratios as those before the amplification by the amplification circuit 34, the DC components S1d and S2d and the AC components S1ar and S2ar can be restored at the same amplitude ratio as that when those components are output from the light receiver 27.

Therefore, the amplitudes ΔS1ar and ΔS2ar of the AC components S1ar and S2ar can be normalized respectively by employing the DC components S1d and S2d and the AC components S1ar and S2ar after being restored, for example.

Accordingly, the arithmetic processing unit 38 can calculate the absorbance ratio R12 based on a ratio of the normalized signal S10, which is obtained as a first ratio of the amplitude ΔS1ar of a first AC component S1ar and a first DC component S1d, to the normalized signal S20, which is obtained as a second ratio of the amplitude ΔS2ar of a second AC component S2ar and a second DC component S2d. As a result, even when the light emission intensity of the light emitting elements 23 and 24 and the light reception sensitivity of the light receiver 27 are different between the first and second wavelength bands, the resultant influence can be reduced and the detection accuracy of the absorbance ratio R12 can be increased.

Figure 8:
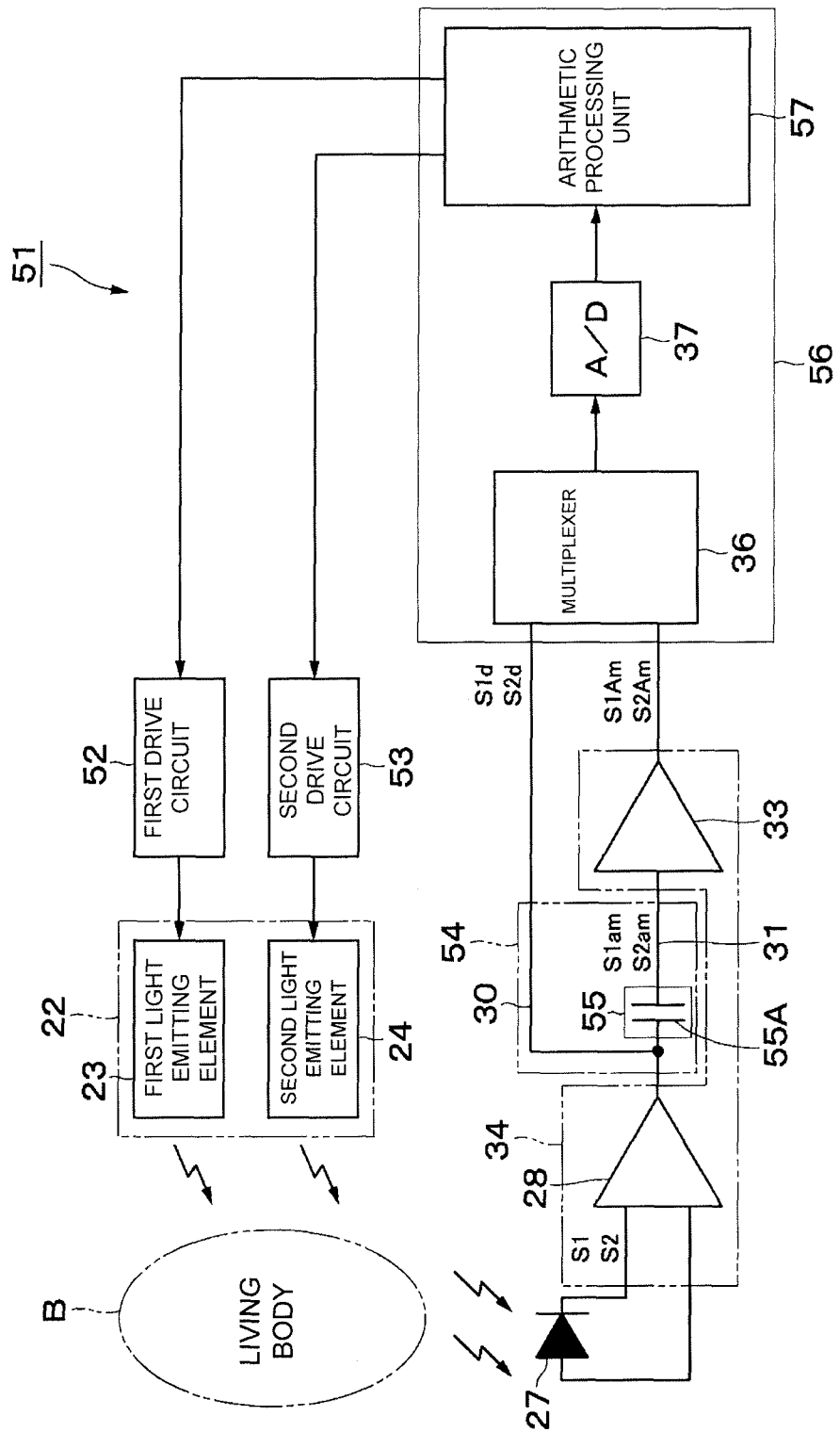
FIG. 8 is an overall block diagram of an optical sensor device according to a third embodiment.

Next, FIG. 8 illustrates a third embodiment of the present invention. The third embodiment is featured in that the light emitter emits light at a predetermined frequency set in advance, and that the separation circuit has, as a passage band, a band including the predetermined frequency of the light emitter and outputs an AC component modulated at the predetermined frequency of the light emitter. It is to be noted that, in the third embodiment, the same constituent elements as those in the second embodiment are denoted by the same reference symbols, and description of those constituent elements is omitted.

An optical sensor device 51 includes, substantially as in the optical sensor device 21 according to the second embodiment, the light emitter 22, first and second drive circuits 52 and 53, the light receiver 27, a separation circuit 54, an the amplification circuit 34, and a processing circuit 56.

Substantially like the first drive circuit 25 in the second embodiment, the first drive circuit 52 is connected to an arithmetic processing unit 57 in the processing circuit 56, and it supplies a drive current to the first light emitting element 23, thereby causing the first light emitting element 23 to emit blinking light. Here, the first drive circuit 52 supplies the drive current that is pulse-modulated at the predetermined frequency f set in advance. The predetermined frequency f is set to a frequency higher than a signal frequency (e.g., about several Hz) of the photo-plethysmographic signal. Preferably, the predetermined frequency f is set to a value (e.g., about several hundreds Hz) higher than the signal frequency of the photo-plethysmographic signal by ten or more times within a range in which the processing circuit 56 is able to execute processing.

In addition, the predetermined frequency f is set to a value (e.g., f=100 Hz) sufficiently lower than the changeover cycle (e.g., 400 Hz) of the AD converter 37 such that conversion to a digital signal can be performed by the AD converter 37.

The second drive circuit 53 also has substantially the same configuration as that of the first drive circuit 52. Thus, the second drive circuit 53 supplies a drive current, which is pulse-modulated at the same predetermined frequency f as that in the first drive circuit 52, to the second light emitting element 24, thereby causing the second light emitting element 24 to emit blinking light. On that occasion, for example, the first and second light emitting elements 23 and 24 may emit the lights at the same timing in synchronism, or may alternately emit the lights at timings different from each other.

The separation circuit 54 also has substantially the same configuration as that of the separation circuit 29 in the second embodiment. Thus, the separation circuit 54 is constituted by first and second branch lines 30 and 31, which are connected in parallel to an output terminal of the preamplifier 28, and by a filter circuit 55, which functions as a high-pass filter connected to an intermediate point of the second branch line 31. The filter circuit 55 is constituted by a capacitor 55A that serves as a coupling capacitor connected between the preamplifier 28 and the post-amplifier 33.

Here, the capacitance of the capacitor 55A is set to a value allowing passage of signals of relatively high frequencies, including the signals having the drive frequency of the light emitting elements 23 and 24. More specifically, the cutoff frequency of the high-pass filter, constituted by the capacitor 55A, is set to a value as high as possible within a range allowing the signal of the predetermined frequency f set for the first and second drive circuits 52 and 53 to pass therethrough.

Because the light emitter 22 emits the lights blinking at the predetermined frequency f, the first and second detection signals S1 and S2 are each a signal obtained with amplitude modulation of the signal of the predetermined frequency f. On that occasion, because the capacitor 55A cuts off signals of lower frequencies than the predetermined frequency f, the filter circuit 55 outputs the first and second AC components S1am and S2am, as modulation signals, which are obtained respectively from the first and second detection signals S1 and S2 through amplitude modulation at the predetermined frequency f. The post-amplifier 33 is an amplifier for amplifying the first and second AC components S1m and S2m which are the modulation signals. Accordingly, the first and second AC components S1am and S2am, both transferred through the second branch line 31, are input to the processing circuit 56 after being amplified respectively to first and second AC components S1Am and S2Am by the post-amplifier 33.

Substantially like the processing circuit 35 in the second embodiment, the processing circuit 56 is mainly constituted by the multiplexer 36, the AD converter 37, and the arithmetic processing unit 57.

Here, the first and second DC components S2d and S2d and the first and second AC components S1Am and S2Am are input to the AD converter 37 in the processing circuit 56 through the multiplexer 36, and the AD converter 37 converts the DC components S1d and S2d and the AC components S1Am and S2Am to digital signals. At that time, the AD converter 37 converts only plus-side values of the AC components S1Am and S2Am to digital signals, for example. The DC components S1d and S2d and the AC components S1Am and S2Am, having been converted to the digital signals, are input to the arithmetic processing unit 57 that is constituted by, e.g., a microcomputer.

Figure 9:
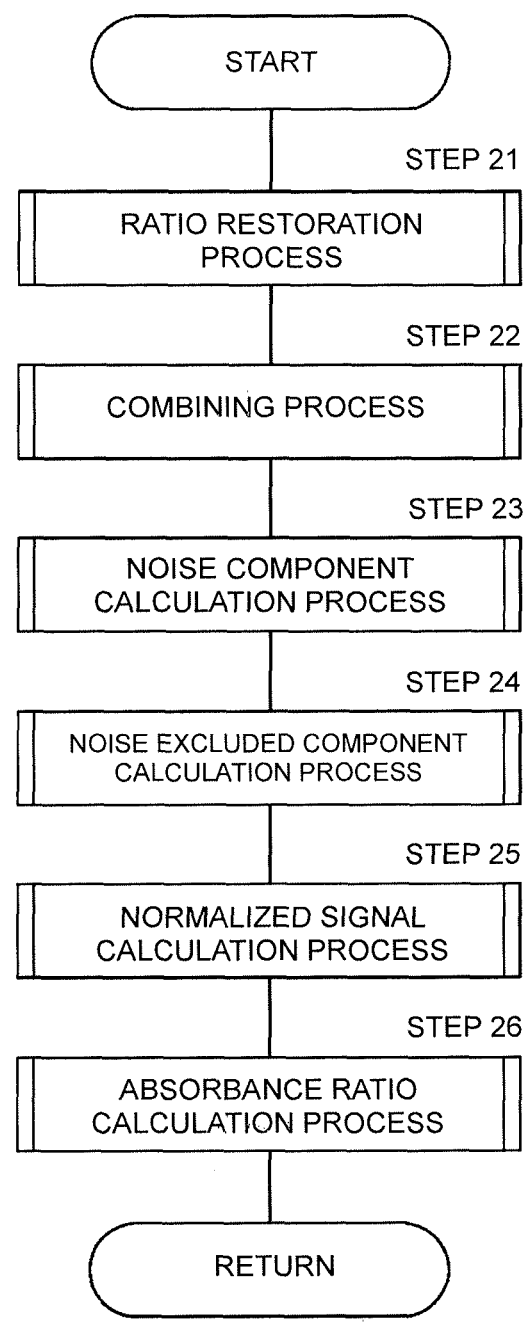
FIG. 9 is a flowchart of a processing program executed by an arithmetic processing unit in FIG. 8.

By executing a processing program illustrated in FIG. 9, the arithmetic processing unit 57 restores the first and second detection signals S1 and S2 before the amplification based on the DC components S1d and S2d and the AC components S1Am and S2Am, which are output from the AD converter 37, and further determines an absorbance ratio R12 of the living body B. In other words, the arithmetic processing unit 57 converts the DC components S1d and S2d and the AC components S1Am and S2Am by employing the amplification factor Gy of the post-amplifier 33 such that amplitude ratios between the DC components S1d and S2d and the AC components S1Am and S2Am come back to the states before the amplification by the post-amplifier 33.

In more detail, the arithmetic processing unit 57 executes a ratio restoration process, illustrated in step 21 of FIG. 9. In step 21, the arithmetic processing unit 57 converts the DC components S1d and S2d and the AC components S1Am and S2Am of the first and second detection signals S1 and S2 based on the amplification factors Gd and Ga such that respective amplitudes of those components are restored to have the same ratios as those before the amplification by the amplification circuit 34. More specifically, the arithmetic processing unit 57 executes arithmetic operations, similar to the above-described formula 3, to calculate restored AC components S1ar and S2ar by dividing the AC components S1Am and S2Am by the amplification factor Gy.

Next, in step 22, a combining process of combining the restored AC components S1ar and S2ar with the DC components S1d and S2d, respectively, is executed. More specifically, the arithmetic processing unit 57 executes arithmetic operations, similar to the above-described formula 4, to obtain first and second restoration signals SR1 and SR2, which are resulted from restoring the first and second detection signals S1 and S2 before the amplification, by adding the restored AC components S1ar and S2ar to the DC components S1d and S2d, respectively.

Figure 10:
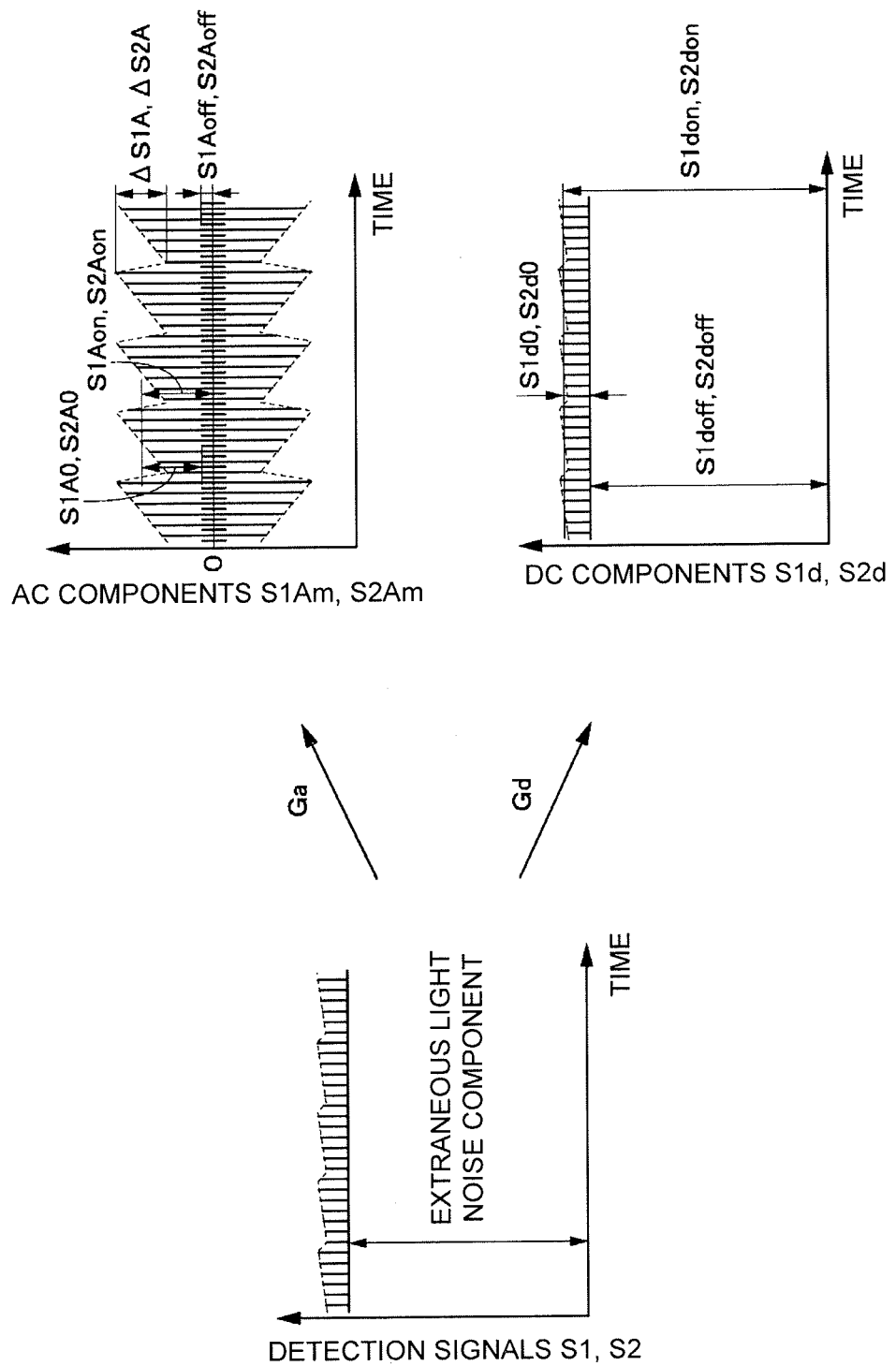
FIG. 10 is an explanatory view illustrating a state where a DC component and an AC component are separated from each of first and second detection signals and are amplified by the optical sensor device in FIG. 8.

As illustrated in FIG. 10, the AC components S1ar and S2ar obtained after amplification correction of the AC components S1Am and S2Am contain the components attributable to the reflected or transmitted lights directly obtained from the living body B. To avoid those components from being superimposed doubly, the first and second restoration signals SR1 and SR2 may be calculated by adding the restored AC components S1ar and S2ar to DC components S1doff and S2doff, which are obtained during the light emission off-periods of the emitting elements 23 and 24 and which are contained in the DC components S1d and S2d, respectively.

Next, in step 23, a noise component calculation process is executed to obtain the DC components S1doff and S2doff attributable to the extraneous light noise by employing the detection signals S1 and S2 during the light emission off-periods of the light emitter 22. More specifically, as illustrated in FIG. 10, when the light emitting elements 23 and 24 do not emit the lights, DC components S1d0 and S2d0 attributable to the lights emitted from the light emitting elements 23 and 24 are not detected, and only the DC components S1doff and S2doff attributable to the extraneous light noise are detected. Therefore, the DC components S1doff and S2doff attributable to the extraneous light noise can be obtained by extracting, from the DC components S1d and S2d, signals obtained during the light emission off-periods of the light emitting elements 23 and 24.

Next, in step 24, a noise excluded component calculation process is executed to obtain the DC components S1d0 and S2d0 excluding the extraneous light noise. More specifically, the detection signals S1 and S2 during the light emission on-periods of the light emitter 22 are extracted to obtain DC components S1don and S2don attributable to not only the extraneous light noise, but also the lights from the light emitting elements 23 the 24, and the DC components S1doff and S2doff attributable to the extraneous light noise are subtracted from the DC components S1don and S2don. As a result, the DC components S1d0 and S2d0 from which the extraneous light noise has been excluded are calculated.

Next, in step 25, a normalized signal calculation process is executed to normalize the amplitudes ΔS1ar and ΔS2ar of the AC components S1ar and S1ar by employing the DC components S1d0 and S2d0, respectively. Here, the amplitudes ΔS1ar and ΔS2ar are ones obtained by restoring the amplitudes ΔS1A and ΔS2A of the AC components S1Am and S2Am after the amplification to the states before the amplification. The normalized signals S10 and S20 are calculated as the first and second ratios by dividing the amplitudes ΔS1ar and ΔS2ar by the DC components S1d0 and S2d0, respectively, in accordance with the following formula 6.

$$S10 = \frac{\Delta S1ar}{S1d0}$$ [Math. 6]

$$S20 = \frac{\Delta S2ar}{S2d0}$$

While, in step 25, the normalized signals S10 and S20 are obtained using the DC components S1d0 and S2d0, the normalized signals S10 and S20 may be obtained based on only the AC components S1Am and S2Am. In such a case, as seen from FIG. 10, values S1A0 and S2A0 corresponding to the DC components excluding the extraneous light noise can be calculated by subtracting, for the AC components S1Am and S2Am, the AC components S1Aoff and S2Aoff during the light emission off-periods from time-average values of the AC components S1Aon and S2Aon during the light emission on-periods of the light emitting elements 23 and 24, respectively. By dividing the amplitudes ΔS1A and ΔS2A of the AC components S1Am and S2Am by the values S1A0 and S2A0, therefore, the amplitudes ΔS1A and ΔS2A can be normalized and the normalized signals S10 and S20 can be obtained.

Next, in step 26, an absorbance ratio calculation process is executed to calculate the absorbance ratio R12 by employing the normalized signals S10 and S20. More specifically, the absorbance ratio R12 is calculated by dividing the normalized signal S10 corresponding to the first wavelength by the normalized signal S20 corresponding to the second wavelength in accordance with the above-described formula 2.

Thus, the third embodiment can also provide similar advantageous effects to those in the second embodiment. According to the third embodiment, particularly, since the light emitter 22 emits the lights at the predetermined frequency f and the separation circuit 54 outputs the AC components S1am and S2am modulated at the predetermined frequency f of the light emitter 22, the cutoff frequency of the separation circuit 54 can be set to a higher value and the capacitance of the capacitor 55A can be reduced.

To explain in more detail, the photo-plethysmographic signal is a low-frequency signal of about several Hz corresponding to the pulse of the living body. To separate the photo-plethysmographic signal, therefore, the cutoff frequency is to be as low as about several Hz, and a capacitor having a large capacitance of, e.g., about several hundreds μF is required. In contrast, in the third embodiment, the separation circuit 54 is just required to allow passage of signals of the predetermined frequency f, which is higher than the frequency of the photo-plethysmographic signal, in order to separate the AC components S1am and S2am modulated at the predetermined frequency f of the light emitter 22. Therefore, the cutoff frequency of the separation circuit 54 can be set to a higher value, and the capacitance of the capacitor 55A can be reduced to be smaller than 1 μF, for example. As a result, reduction in size and cost can be realized.

Furthermore, the DC components S1doff and S2doff attributable to the extraneous light noise alone can be extracted by employing digital signal data of the DC components S1d and S2d during the light emission off-periods. Thus, since the DC components S1doff and S2doff attributable to the extraneous light noise can be excluded respectively from the detected DC components S1d and S2d, the amplitudes ΔS1ar and ΔS2ar of the AC components S1ar and S2ar can be normalized without suffering from the influence of the extraneous light noise. As a result, the absorbance ratio R12 of the living body B can be obtained with high accuracy.

In the second and third embodiments described above, step 11 in FIG. 5 and step 21 in FIG. 9 represent practical examples of ratio restoration means. Step 14 in FIG. 5 and step 26 in FIG. 9 represent practical examples of absorbance ratio calculation means. Step 23 in FIG. 9 represents a practical example of noise component calculation means.

While, in each of the above-described embodiments, the light emitters 2 and 22 are each configured to emit the lights of two different wavelengths, they may be each configured to emit light of one wavelength or lights of three or more wavelengths.

Moreover, the foregoing embodiments have been each described above in connection with an example in which the present invention is applied to the optical sensor device 1, 21 or 51 for detecting the photo-plethysmographic signal of the living body B. However, application fields of the present invention are not limited to that type of optical sensor device, and the present invention can be applied to various types of optical sensor devices for detecting lights reflected by or transmitted through measurement targets.

REFERENCE SIGNS LIST 1, 21, 51 optical sensor devices
2, 22 light emitters
3, 4, 23, 24 light emitting elements
7, 27 light receivers
9, 32, 55 filter circuits
10, 33 post-amplifiers (amplifiers)
11, 34 amplification circuits
14, 37 AD converters
15, 38, 57 arithmetic processing units
29, 54 separation circuits

The invention claimed is:
1. An optical sensor device comprising:
a light emitter configured to periodically emit light at a predetermined frequency toward a measurement target;
a light receiver configured to detect at least one of reflected light and diffused light from the measurement target, and to output an electrical signal based on the detected light;
a filter circuit configured to filter the electrical signal at the predetermined frequency and to output a modulation signal;
an amplifier configured to amplify the modulation signal;
an AD converter configured to convert the modulation signal to a digital signal; and
an arithmetic processing unit coupled to the AD converter and configured to calculate a DC component of the electrical signal based on the digital signal by:
calculating a total DC component based on both extraneous light noise and the detected light by employing a signal contained in the modulation signal and obtained during an on-period of the light emitter,
calculating a DC component attributable to the extraneous light noise by employing a signal contained in the modulation signal and obtained during an off-period of the light emitter, and
calculating the DC component attributable to the detected light by excluding the DC component attributable to the extraneous light noise from the calculated total DC component,
wherein the arithmetic processing unit is further configured to calculate an AC component of the electrical signal by excluding the DC component from the modulation signal.

2. The optical sensor device according to claim 1, wherein the filter circuit comprises a frequency band that corresponds to a portion of the electrical signal.

3. The optical sensor device according to claim 1, wherein the light emitter comprises:
 a first light emitting element configured to emit light in a first wavelength band at the predetermined frequency; and
 a second light emitting element configured to emit light in a second wavelength band at the predetermined frequency, the second wavelength band being different than the first wavelength band.

4. The optical sensor device according to claim 3, wherein the first and second light emitting elements are configured to concurrently emit light at the predetermined frequency.

5. The optical sensor device according to claim 3, wherein the first and second light emitting elements are configured to alternately emit light at the predetermined frequency.

6. The optical sensor device according to claim 3, wherein the light receiver is further configured to detect light in both the first and second wavelength bands and to output a first electrical signal and a second electrical signal corresponding to light emitted from the first and second light emitting elements, respectively.

7. The optical sensor device according to claim 6, wherein the arithmetic processing unit is further configured to calculate an absorbance ratio of the measurement target based on a ratio of a first ratio between an amplitude of a first AC component and a first DC component calculated from the first electrical signal, to a second ratio between an amplitude of a second AC component and a second DC component calculated from the second electrical signal.

8. The optical sensor device according to claim 1, further comprising:
 a separation circuit including the filter circuit and configured to separate the modulation signal and the DC component of the electrical signal,
 wherein the AD converter is further configured to convert the DC component of the electrical signal to a DC component digital signal, and
 wherein the arithmetic processing unit is further configured to convert the modulation signal and the DC component digital signal based on an amplification factor of the amplifier, such that an amplitude ratio between the modulation signal and the DC component digital signal reaches a state before the amplification by the amplifier, and to calculate the AC component of the electrical signal based on the modulation signal.

9. The optical sensor device according to claim 8, wherein the arithmetic processing unit is further configured to calculate the DC component attributable to extraneous light noise based on a signal contained in the DC component of the electrical signal and obtained during an off-period of the light emitter.

10. An optical sensing method comprising:
 emitting light, by a light emitter, at a predetermined frequency towards a measurement target;
 detecting, by a light receiver, at least one of reflected light and diffused light from the measurement target;
 outputting, by the light receiver, an electrical signal based on the detected light;
 filtering, by a filter circuit, the electrical signal at the predetermined frequency;
 outputting, by the filter circuit, a modulation signal corresponding to the filtered electrical signal;
 amplifying, by an amplifier, the modulation signal;
 converting, by an AD converter, the amplified modulation signal to a digital signal;
 calculating, by a processor, a DC component and an AC component of the electrical signal based on the digital signal, wherein the DC component of the electrical signal is calculated by determining a time-average value of the modulation signal and the AC component of the electrical signal is calculated by excluding the DC component from the modulation signal;
 calculating, by the processor, a total DC component based on both extraneous light noise and the detected light by employing a signal contained in the modulation signal and obtained during an on-period of the light emitter;
 calculating, by the processor, a DC component attributable to the extraneous light noise by employing a signal contained in the modulation signal and obtained during an off-period of the light emitter; and
 calculating, by the processor, the DC component attributable to the detected light by excluding the DC component attributable to the extraneous light noise from the calculate total DC component.

11. The optical sensing method according to claim 10, further comprising:
 separating, by a separation circuit including the filter circuit, the modulation signal and the DC component of the electrical signal;
 converting, by the AD converter, the DC component of the electrical signal to a DC component digital signal;
 converting, by the processor, the modulation signal and the DC component digital signal based on an amplification factor of the amplifier, such that an amplitude ratio between the modulation signal and the DC component digital signal reaches a state before the amplification by the amplifier; and
 calculating, by the processor, the AC component of the electrical signal based on the modulation signal.

12. The optical sensing method according to claim 11, further comprising calculating, by the processor, the DC component attributable to extraneous light noise based on a signal contained in the DC component of the electrical signal and obtained during an off-period of the light emitter.

13. The optical sensing method according to claim 10, wherein the step of emitting light further comprises:
 emitting, by a first light emitting element of the light emitter, light in a first wavelength band at a predetermined frequency towards the measurement target; and
 emitting, by a second light emitting element of the light emitter, light in a second wavelength band at the predetermined frequency towards the measurement target,
 wherein the step of outputting the electrical signal comprises outputting, by the light receiver, first and second electrical signal based on the detected light in the first and second wavelength bands, respectively, and
 wherein the step of calculating the DC component and AC component comprises:
  calculating, by the processor, a first DC component and a first AC component of the first electrical signal; and
  calculating, by the processor, a second DC component and a second AC component of the second electrical signal.

14. The optical sensing method according to claim 13, wherein the steps of emitting light in the first and second wavelength bands is performed either concurrently at the predetermined frequency or alternately at the predetermined frequency.

15. The optical sensing method according to claim 13, further comprising calculating, by the processor, an absorbance ratio of the measurement target based on a ratio of a first ratio between an amplitude of the first AC component and the first DC component, to a second ratio between an amplitude of the second AC component and the second DC component.

* * * * *